(12) United States Patent  
Matsui (10) Patent No.: US 10,588,555 B2
(45) Date of Patent: Mar. 17, 2020

(54) PULSE OXIMETER

(71) Applicant: PIONEER CORPORATION, Tokyo (JP)

(72) Inventor: Yutaka Matsui, Kanagawa (JP)

(73) Assignee: PIONEER CORPORATION, Tokyo (JP)

( * ) Notice: Subject to any disclaimer, the term of this patent is extended or adjusted under 35 U.S.C. 154(b) by 496 days.

(21) Appl. No.: 15/311,931

(22) PCT Filed: May 20, 2014

(86) PCT No.: PCT/JP2014/063356
§ 371 (c)(1),
(2) Date: Nov. 17, 2016

(87) PCT Pub. No.: WO2015/177867
PCT Pub. Date: Nov. 26, 2015

(65) Prior Publication Data
US 2017/0119293 A1 May 4, 2017

(51) Int. Cl.
*A61B 5/1455* (2006.01)
*A61B 5/0205* (2006.01)
(Continued)

(52) U.S. Cl.
CPC ........ *A61B 5/14551* (2013.01); *A61B 5/0205* (2013.01); *A61B 5/14546* (2013.01);
(Continued)

(58) Field of Classification Search
CPC .............. A61B 5/14551; A61B 5/0205; A61B 5/14546; A61B 5/6826; A61B 5/6843; A61B 5/024; A61B 5/02416; A61B 5/72
See application file for complete search history.

(56) References Cited

U.S. PATENT DOCUMENTS 5,111,817 A * 5/1992 Clark ................. A61B 5/02007
356/41
5,485,838 A * 1/1996 Ukawa ................... A61B 5/022
356/41
(Continued)

FOREIGN PATENT DOCUMENTS

JP          06-63024        3/1994
JP        2007-330708      12/2007
(Continued)

OTHER PUBLICATIONS

International Search Report, PCT/JP2014/063356, dated Jul. 8, 2014.

*Primary Examiner* — Eric F Winakur
(74) *Attorney, Agent, or Firm* — Young & Thompson (57) ABSTRACT

A pulse oximeter (1, 2) includes a first light emitter (11) configured to generate first light, a second light emitter (12) configured to generate second light with a different wavelength from that of the first light, and a light receiver (13) configured to receive each of first return light of the first light from a living body and second return light of the second light from the living body. The pulse oximeter is provided with: a contact pressure detecting device (14) configured to detect a signal associated with contact pressure between the pulse oximeter and the living body; and an outputting device (100) configured to output information regarding oxygen saturation, on the basis of respective signals outputted from the light receiver due to the first return light and the second return light, and the detected signal associated with the contact pressure.

2 Claims, 9 Drawing Sheets

(51) Int. Cl.
*A61B 5/145* (2006.01)
*A61B 5/00* (2006.01)
*A61B 5/024* (2006.01)

(52) U.S. Cl.
CPC .......... *A61B 5/6826* (2013.01); *A61B 5/6843* (2013.01); *A61B 5/024* (2013.01); *A61B 5/02416* (2013.01); *A61B 5/72* (2013.01)

(56) References Cited

U.S. PATENT DOCUMENTS

| | | | |
|---|---|---|---|
| 5,601,079 A * | 2/1997 | Wong | A61B 5/14532 600/322 |
| 7,039,454 B1 | 5/2006 | Kaga et al. | |
| 7,613,488 B1 * | 11/2009 | Maracas | A61B 5/14532 600/322 |
| 2006/0184044 A1 | 8/2006 | Kaga et al. | |
| 2007/0208238 A1 * | 9/2007 | Harjunmaa | A61B 5/14532 600/316 |
| 2009/0204009 A1 * | 8/2009 | Powers | A61B 5/0075 600/476 |
| 2010/0056880 A1 | 3/2010 | Cho et al. | |
| 2010/0076282 A1 * | 3/2010 | Sandmore | A42B 1/242 600/340 |
| 2010/0222652 A1 | 9/2010 | Cho et al. | |
| 2012/0136228 A1 | 5/2012 | Kobayashi et al. | |
| 2015/0335293 A1 * | 11/2015 | Christman | A61B 5/6897 600/324 |

FOREIGN PATENT DOCUMENTS

| | | |
|---|---|---|
| JP | 2009-233374 | 10/2009 |
| JP | 2010-537751 | 12/2010 |
| JP | 2012-110520 | 6/2012 |

* cited by examiner

FIG. 3A
Mounting Pressure: Low

FIG. 3B
Mounting Pressure: Middle

FIG. 3C
Mounting Pressure: High

FIG. 7A
No Correction of Mounting Pressure

FIG. 7B
After Correction of Mounting Pressure

FIG. 12

PULSE OXIMETER

TECHNICAL FIELD

The present invention relates to a pulse oximeter.

BACKGROUND ART

For this type of pulse oximeter, on the premise that it is always worn, there has been proposed a ring-type pulse oximeter configured to press a measurement object portion to increase pulsation of arteries, for example, if there are few detectable pulsation components, or if vasoconstriction caused by low body temperature reduces measurement accuracy of oxygen saturation, or in similar cases (refer to Patent Literature 1).

Alternatively, there has been proposed an apparatus configured to simultaneously and continuously measure blood pressure and blood oxygen saturation, by obtaining a blood pressure value on the basis of the pulsation component and cuff pressure of one of two volume signals according to lights with different wavelengths, and by obtaining blood oxygen saturation from volume pulse wave signals extracted from respective pulsation components of the two volume signals (refer to Patent Literature 2).

CITATION LIST

Patent Literature

Patent Literature 1: Japanese Patent Application Laid Open No. 2007-330708
Patent Literature 2: Japanese Patent Application Laid Open No. Hei 6-63024

SUMMARY OF INVENTION

Technical Problem

By the way, in measurement of arterial oxygen saturation (hereinafter referred to as "$SpO_2$" as occasion demands) by the pulse oximeter, a measurement result of $SpO_2$ changes if mounting pressure of a sensor, which constitutes the pulse oximeter, changes.

In the technology described in the Patent Literature 1, if the mounting pressure of the sensor of the ring-type pulse oximeter is relatively high, for example, because of swelling of a finger of an object person or the like, then, there is a possibility that a $SpO_2$ value cannot be accurately measured, which is technically problematic. Moreover, in the technology described in the Patent Literature 2, the mounting pressure of the sensor is not considered in the $SpO_2$ measurement.

In view of the aforementioned problems, it is therefore an object of the present invention to provide a pulse oximeter configured to suppress an influence of the mounting pressure of a sensor.

Solution to Problem

The above object of the present invention can be achieved by a first pulse oximeter including a first light emitter configured to generate first light, a second light emitter configured to generate second light with a different wavelength from that of the first light, and a light receiver configured to receive each of first return light of the first light from a living body and second return light of the second light from the living body, said pulse oximeter is provided with: a contact pressure detecting device configured to detect a signal associated with contact pressure between said pulse oximeter and the living body; and an outputting device configured to output information regarding oxygen saturation, on the basis of respective signals outputted from the light receiver due to the first return light and the second return light, and the detected signal associated with the contact pressure.

The above object of the present invention can be achieved by a second pulse oximeter including a first light emitter configured to generate first light, a second light emitter configured to generate second light with a different wavelength from that of the first light, and a light receiver configured to receive each of first return light of the first light from a living body and second return light of the second light from the living body, said pulse oximeter is provided with: a contact pressure detecting device configured to detect a signal associated with contact pressure between said pulse oximeter and the living body; and an outputting device configured to output information regarding adjustment of the contact pressure in accordance with the detected signal associated with the contact pressure.

The operation and other advantages of the present invention will become more apparent from embodiments and examples explained below.

DESCRIPTION OF EMBODIMENTS

Hereinafter, a pulse oximeter according to the present invention will be explained.

First Embodiment

A pulse oximeter according to a first embodiment includes a first light emitter, a second light emitter, and a light receiver. The first light emitter generates first light. The second light emitter generates second light with a different wavelength from that of the first light. Here, it is desirable, but not limited to, that the wavelength of one of the first light and the second light is a wavelength that is superior in absorption into oxygenated hemoglobin, and the wavelength of the other light of the first light and the second light is a wavelength that is superior in absorption into deoxygenated hemoglobin. The pulse oximeter according to the embodiment may be provided with three or more light emitters.

The light receiver receives each of first return light of the first light from a living body and second return light of the second light from the living body. Here, the "return light" conceptually includes not only light scattered or reflected by the living body, but also light transmitted through the living body. In other words, the pulse oximeter according to the embodiment may be a reflection type pulse oximeter, or may be a transmission type pulse oximeter. The light receiver may be provided not only with a single light emitting element, but also with a plurality of light emitting elements.

A contact pressure detecting device detects a signal associated with contact pressure between the pulse oximeter and the living body. Here, the "signal associated with the contact pressure" is not limited to a signal indicating the contact pressure itself, but also conceptually includes an output signal of a sensor, such as, for example, a pressure sensor, a signal indicating physical quantity or parameters indirectly indicating the contact pressure, or the like.

An outputting device, which is provided, for example, with a memory, a processor, and the like, outputs information regarding oxygen saturation, on the basis of respective signals outputted from the light receiver due to the first return light and the second return light, and the detected signal associated with the contact pressure. Here, the "information regarding the oxygen saturation" is not limited to information indicting the oxygen saturation itself, but also conceptually includes information indirectly indicating the oxygen saturation, such as, for example, information indicating a ratio between return light of red light and return light of infrared light.

According to the study of the present inventors, the following matter has been found. The pulse oximeter outputs the information regarding the oxygen saturation on the basis of pulsation components of the output signals of the light receiver, which are caused by arterial blood. Here, blood vessels that pulsate in the living body are only arteries, and pulsation does not occur in veins, which come from capillaries and in which the blood pressure is low enough to be regarded as 0 mmHg. In reality, however, the pulsation of the arteries propagates in living tissues, and physically vibrates the veins. As a result, the pulsation components of the output signals of the light receiver include information about the veins to a greater or lesser extent.

If the contact pressure of the pulse oximeter against the living body changes, a physical distance between the arteries and the veins in the living body changes, and an influence of the pulsation of the arteries on the veins also changes. In other words, the change in the contact pressure also changes an influence of the veins on the pulsation components of the output signals. In many cases, the pulse oximeter is designed to obtain accurate oxygen saturation, on the assumption of the contact pressure. Thus, depending on the contact pressure, there is a significant influence of the veins on the pulsation components of the output signals, and inaccurate oxygen saturation is possibly obtained.

Thus, in the embodiment, the information regarding the oxygen saturation is outputted by the outputting device on the basis of the respective signals outputted from the light receiver due to the first return light and the second return light, and the detected signal associated with the contact pressure.

Specifically, for example, the outputting device corrects the respective signals outputted from the light receiver due to the first return light and the second return light (e.g. increases or reduces signal amplitude), in accordance with the detected signal associated with the contact pressure, and outputs the information regarding the oxygen saturation. Alternatively, the outputting device corrects the information regarding the oxygen saturation, which is obtained on the basis of the respective signals outputted from the light receiver due to the first return light and the second return light, in accordance with the detected signal associated with the contact pressure. In either way, the information regarding the oxygen saturation with no or little influence of the contract pressure thereon is outputted.

As a result, according to the pulse oximeter in the embodiment, it is possible to suppress the influence of the contact pressure, and it is thus possible to output the information regarding the oxygen saturation with high reliability.

In one aspect of the pulse oximeter according to the first embodiment, the outputting device changes an amplification factor associated with at least one of the signal outputted from the light receiver due to the first return light and the signal outputted from the light receiver due to the second return light, on the basis of the detected signal associated with the contact pressure.

For example, if the contact pressure increases, the physical distance between the arteries and the veins in the living body decreases, and the influence of the pulsation of the arteries on the veins increases. Then, due to an influence of the veins, the pulsation components (or signal amplitude) of the output signals become high.

The outputting device changes the amplification factor associated with at least one of the signal outputted from the light receiver due to the first return light and the signal outputted from the light receiver due to the second return light, on the basis of the detected signal associated with the contact pressure, as described above, by which the influence of the veins (i.e. the influence of the contact pressure) can be suppressed or removed.

Alternatively, in another aspect of the pulse oximeter according to the first embodiment, the pulse oximeter is further provided with a second outputting device configured to output information associated with adjustment of the contact pressure in accordance with the detected signal associated with the contact pressure.

According to this aspect, if the contact pressure of the pulse oximeter is adjusted automatically or manually in accordance with the outputted information regarding the adjustment of the contact pressure, it is possible to output the information regarding the oxygen saturation with the influence of the contact pressure suppressed.

The "information regarding the adjustment of the contact pressure" is not limited to information indicating an adjustment value of the contact pressure itself, but also conceptually includes information indirectly encouraging the adjustment of the contact pressure, such as, for example, "the contact pressure is high" and "the contact pressure is low", physical quantity or parameters directly or indirectly indicating the extent of the contact pressure, or the like.

Second Embodiment

A pulse oximeter according to a second embodiment includes a first light emitter, a second light emitter, and a light receiver. The first light emitter generates first light. The second light emitter generates second light with a different wavelength from that of the first light. The light receiver receives each of first return light of the first light from a living body and second return light of the second light from the living body.

A contact pressure detecting device detects a signal associated with contact pressure between the pulse oximeter and the living body. An outputting device, which is provided, for example, with a memory, a processor, and the like, outputs information regarding adjustment of the contact pressure in accordance with the detected signal associated with the contact pressure.

If the contact pressure of the pulse oximeter is adjusted automatically or manually in accordance with the outputted information regarding the adjustment of the contact pressure, the oxygen saturation is measured in appropriate contact pressure. As a result, it is possible to obtain the oxygen saturation, with an influence of the contact pressure suppressed.

In one aspect of the pulse oximeter according to the second embodiment, the pulse oximeter is further provided with an adjusting device configured to adjust the contact pressure between the pulse oximeter and the living body, in accordance with the outputted information regarding the adjustment of the contact pressure.

According to this aspect, the contact pressure is automatically adjusted, which is extremely useful in practice.

EXAMPLES

A pulse oximeter according to examples of the present invention will be explained with reference to the drawings.

First Example

A pulse oximeter according to a first example of the present invention will be explained with reference to FIG. 1 to FIG. 7.

Figure 1:
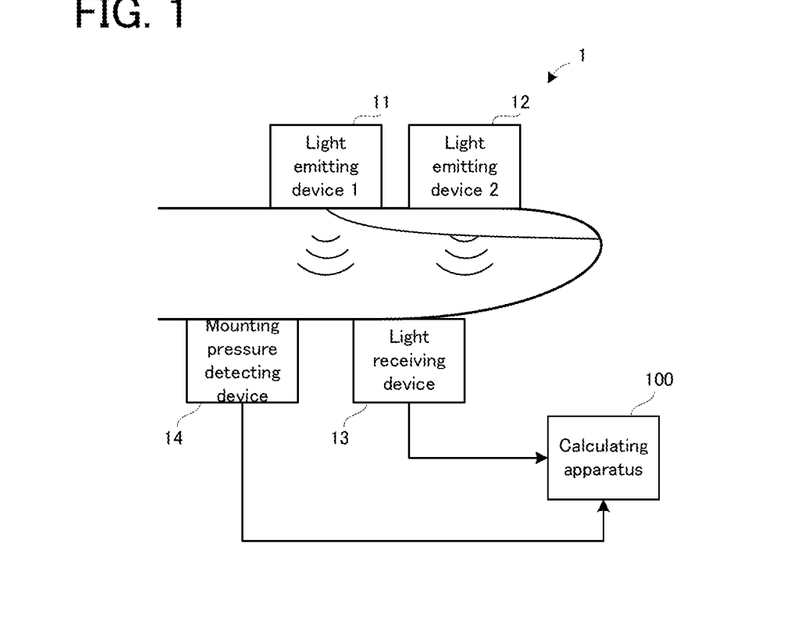
FIG. 1 is a schematic block diagram illustrating an outline of a pulse oximeter according to a first example.

In FIG. 1, a pulse oximeter 1 is provided with a light emitting device 11, a light emitting device 12, a light receiving device 13, such as, for example, a photodiode (PD), a mounting pressure detecting device 14, such as, for example, a pressure sensor, and a calculating apparatus 100 configured to process a signal outputted from the light receiving device 13 and a signal outputted from the mounting pressure detecting device 14.

The light emitting device 11 is provided, for example, with an infrared light emitting diode (LED), and generates first light with a wavelength that is superior in absorption into oxygenated hemoglobin. On the other hand, the light emitting device 12 is provided, for example, with a red light LED, and is configured to generate second light with a wavelength that is superior in absorption into deoxygenated hemoglobin.

The first light and the second light are applied to blood vessels of a human's finger (corresponding to the "living body" according to the present invention). The light receiving device 13 mainly receives first transmitted light (corresponding to the "first return light" according to the present invention) of the first light transmitted through the blood vessels and second transmitted light (corresponding to the "second return light" according to the present invention) of the second light transmitted through the blood vessels, and outputs a signal according to the amount of light received.

Here, $SpO_2$ is obtained on the basis of an amplitude ratio between a signal outputted from the light receiving device 13 due to the first transmitted light (i.e. the light with the wavelength that is superior in absorption into the oxygenated hemoglobin) and a signal outputted from the light receiving device 13 due to the second transmitted light (i.e. the light with the wavelength that is superior in absorption into the deoxygenated hemoglobin).

By the way, it has been found by the study of the present inventors that amplitude of the signal outputted from the light receiving device 13 is influenced by mounting pressure of the pulse oximeter 1. Specifically, for example, as illustrated in FIG. 3 and FIG. 4, the amplitude of the signal outputted from the light receiving device 13 changes depending on the mounting pressure of the pulse oximeter.

Figure 3A:
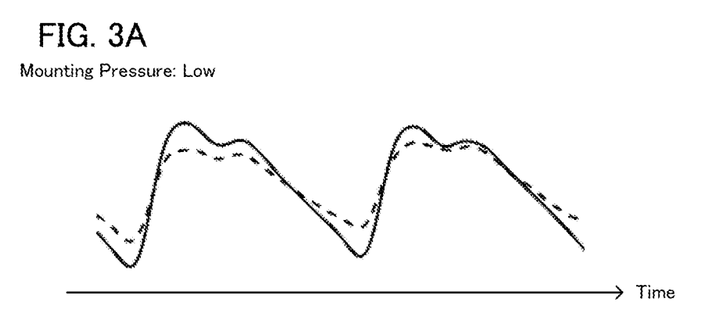
FIG. 3A to FIG. 3C are diagrams illustrating one example of signals outputted from a light receiver, for each mounting pressure.
Figure 3B:
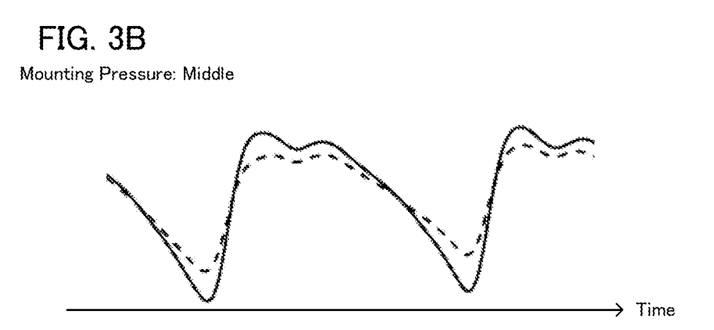
Figure 3C:
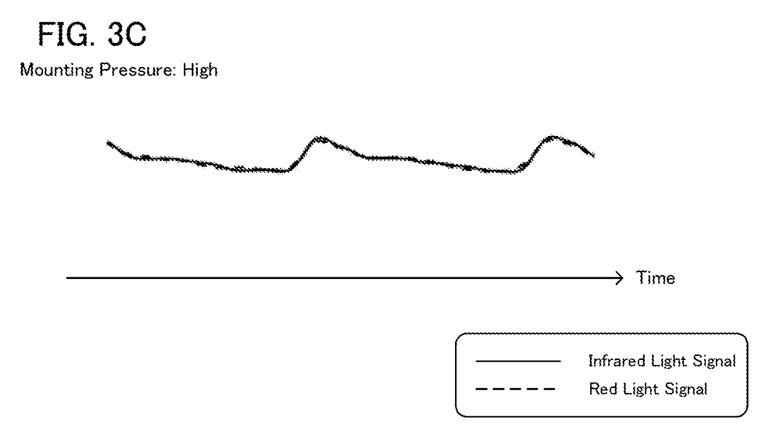
Figure 4:
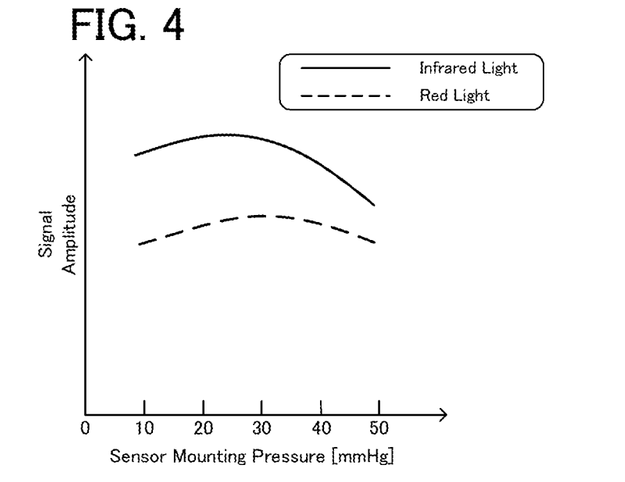
FIG. 4 is a characteristic diagram illustrating one example of a relation between the mounting pressure and signal amplitude.

An "infrared light signal" and a "red light signal" in FIG. 3 and FIG. 4 respectively correspond to the "signal outputted from the light receiving device 13 due to the first transmitted light" and the "signal outputted from the light receiving device 13 due to the second transmitted light".

In particular, if the mounting pressure of the pulse oximeter 1 becomes high, venous blood causes an increase in a ratio at which the second light with the wavelength that is superior in absorption into the deoxygenated hemoglobin is absorbed into the living body. Then, the amplitude of the signal outputted from the light receiving device 13 due to the second light (or the second transmitted light) hardly decreases in comparison with the amplitude of the signal outputted from the light receiving device 13 due to the first transmitted light (refer to FIG. 4).

Figure 5:
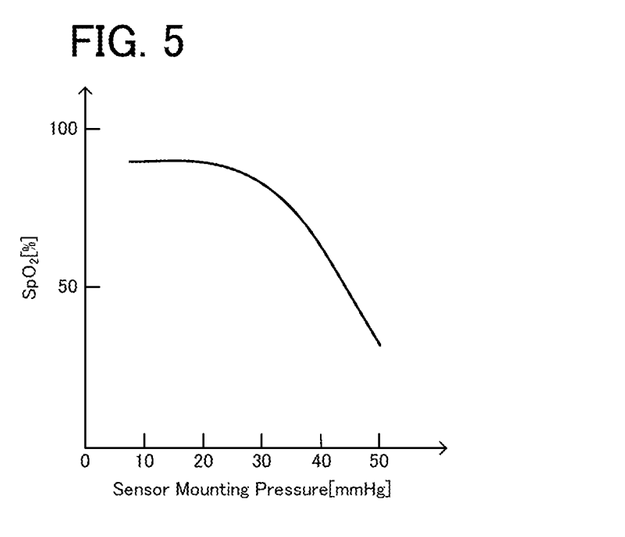
FIG. 5 is a characteristic diagram illustrating one example of a relation between the mounting pressure and $SpO_2$.

As a result, a ratio between the amplitude of the signal outputted from the light receiving device 13 due to the first transmitted light and the amplitude of the signal outputted from the light receiving device 13 due to the second transmitted light becomes relatively small. Thus, if no measures are taken, as illustrated in FIG. 5, a value of $SpO_2$ remarkably decreases as the mounting pressure of the pulse oximeter 1 increases (namely, an inaccurate value of $SpO_2$ is possibly outputted).

Thus, in the example, in order to suppress an influence of a vein, an amplification factor of the signal outputted from the light receiving device 13 due to the second transmitted light is changed by the calculating apparatus 100 in accordance with the signal outputted from the mounting pressure detecting device 14 (corresponding to the "signal associated with the mounting pressure" according to the present invention). Then, $SpO_2$ is obtained by the calculating apparatus 100 on the basis of an amplitude ratio between a signal caused by the second transmitted light with the amplification factor changed and the signal outputted from the light receiving device 13 due to the first transmitted light.

Figure 2:
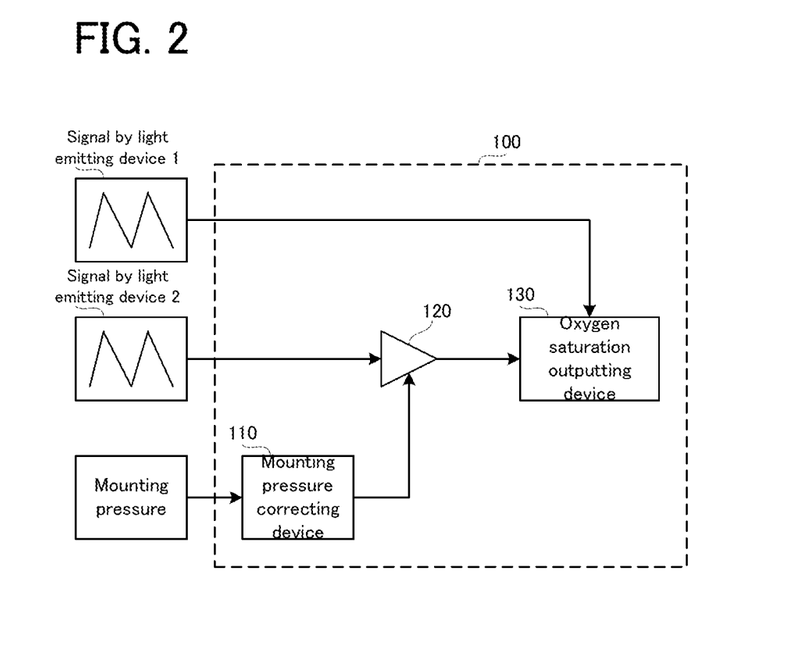
FIG. 2 is a block diagram illustrating a main part of a calculating apparatus according to the first example.

Specifically, in FIG. 2, the calculating apparatus 100 is provided with a mounting pressure correcting device 110, an amplifier 120, and an oxygen saturation outputting device 130.

The mounting pressure correcting device 110 determines a correction coefficient of the amplification factor associated with the amplifier 120 in accordance with the signal associated with the mounting pressure outputted from the mounting pressure detecting device 14.

The correction coefficient is determined, for example, by using a difference $\Delta p$ between actual mounting pressure based on the signal associated with the mounting pressure outputted from the mounting pressure detecting device 14 and preset standard mounting pressure, and by using a function F(Δp) of the difference Δp.

Figure 6:
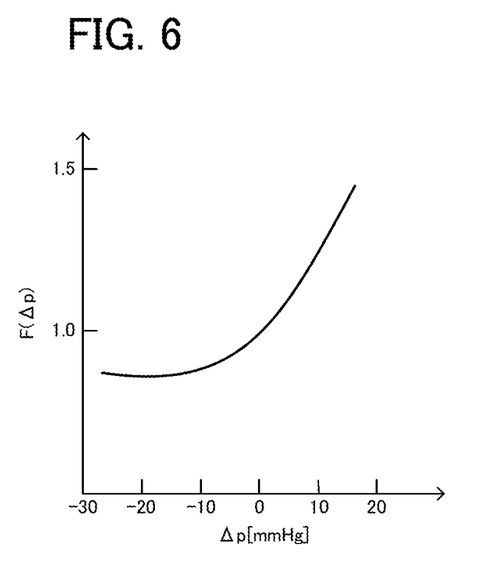
FIG. 6 is a diagram illustrating one example of a correction function $F(\Delta p)$ of an amplification factor according to the first example.

The function F(Δp) may be obtained as an approximate curve regarding a plurality of ratios obtained, wherein each of the obtained ratios is a ratio between an amplitude ratio that is between the signal caused by the first transmitted light and the signal caused by the second transmitted light in the standard mounting pressure, and an amplitude ratio that is between the signal caused by the first transmitted light and the signal caused by the second transmitted light in arbitrary mounting pressure (refer to FIG. 6).

In other words, the function F(Δp) can be expressed in the following numerical expression.

$$\frac{RD_{std}}{IR_{std}} \bigg/ \frac{RD}{IR} = F(\Delta p) \qquad [\text{Eq 1}]$$

wherein $RD_{std}$ is an amplitude value of the signal caused by the second transmitted light in the standard mounting pressure, $IR_{std}$ is an amplitude value of the signal caused by the first transmitted light in the standard mounting pressure, RD is an amplitude value of the signal caused by the second transmitted light in arbitrary mounting pressure, and IR is an amplitude value of the signal caused by the first transmitted light in arbitrary mounting pressure.

If the above numerical expression is transformed, the amplitude ratio between the signal caused by the second transmitted light and the signal caused by the first transmitted light in the standard mounting pressure (in other words, in appropriate mounting pressure) can be obtained by using the function F(Δp) and the amplitude ratio between the signal caused by the second transmitted light and the signal caused by the first transmitted light actually outputted (i.e. in arbitrary mounting pressure) (refer to the following numerical expression).

$$\frac{RD_{std}}{IR_{std}} = \frac{RD}{IR} = \times F(\Delta p) \qquad [\text{Eq 2}]$$

In accordance with the above numerical expression, the mounting pressure correcting device 110 determines a value of F(Δp) obtained on the basis of the signal associated with the mounting pressure outputted from the mounting pressure detecting device 14, to be the correction coefficient of the amplification factor associated with the amplifier 120.

The amplification factor associated with the amplifier 120 is changed in accordance with the correction coefficient determined by the mounting pressure correcting device 110, by which the amplitude of the signal caused by the second transmitted light (corresponding to "RD" in the above equation) is changed. The oxygen saturation outputting device 130 obtains $SpO_2$ on the basis of the signal caused by the second transmitted light with the amplitude changed and the signal caused by the first transmitted light.

Figure 7A:
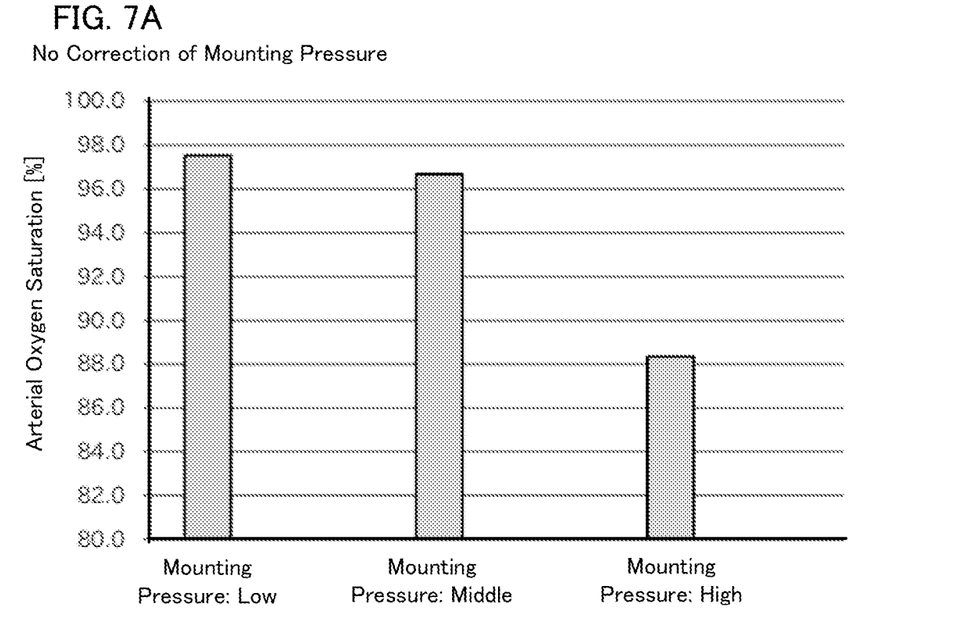
FIG. 7A and FIG. 7B are diagrams illustrating one example of a measurement result of $SpO_2$ in no correction and one example of a measurement result of $SpO_2$ in correction.
Figure 7B:
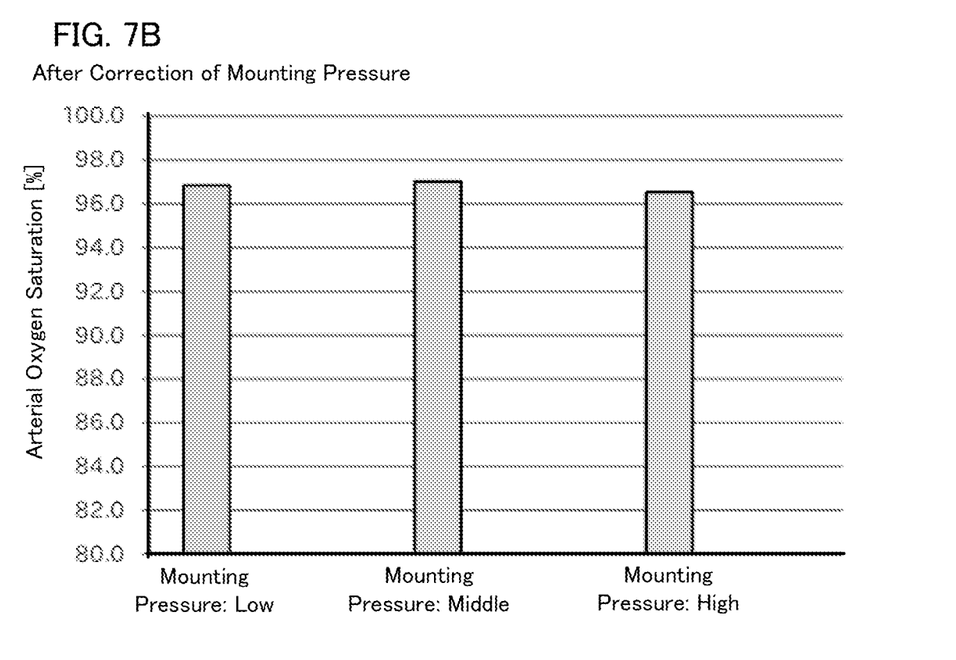

If no measures are taken for the mounting pressure of the pulse oximeter 1, a measurement result of $SpO_2$ is, for example, as illustrated in FIG. 7A. In the example, however, as described above, the amplification factor of the signal caused by the second transmitted light is corrected in accordance with the mounting pressure of the pulse oximeter 1, and thus, for example, a measurement result as illustrated in FIG. 7B is obtained. In other words, according to the pulse oximeter 1 in the example, the obtained measurement result is that there is no or little influence of the mounting pressure.

The light emitting device 11 and the light emitting device 12 are driven in a temporally alternate manner (in other words, the first light and the second light are generated in a temporally alternate manner). Then, for example, the calculating apparatus 100 is provided with a switching circuit (not illustrated), which is configured to input the signal outputted from the light receiving device 13 directly to the oxygen saturation outputting device 130 in a driving period of the light emitting device 11 and which is configured to input the signal outputted from the light receiving device 13 to the oxygen saturation outputting device 13 via the amplifier 120 in a driving period of the light emitting device 12.

Figure 8A:
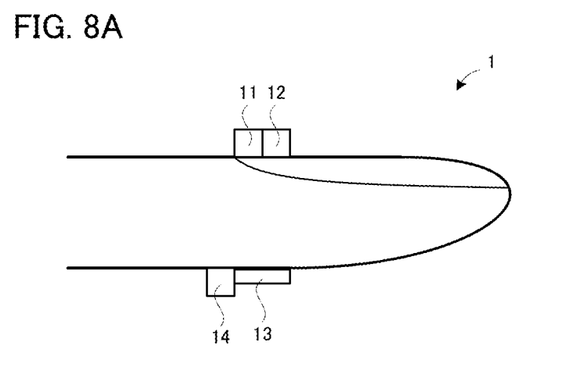
FIG. 8A to FIG. 8C are diagrams illustrating arrangement examples of elements that constitute a transmission type pulse oximeter according to the first example.
Figure 8B:
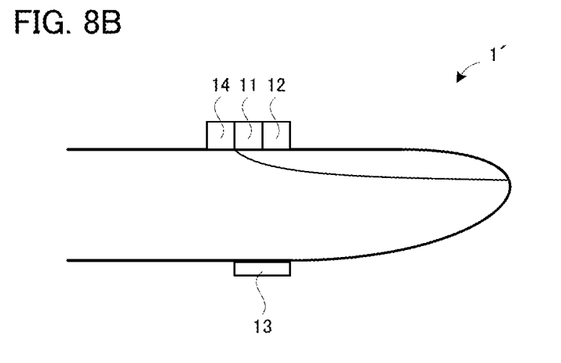
Figure 8C:
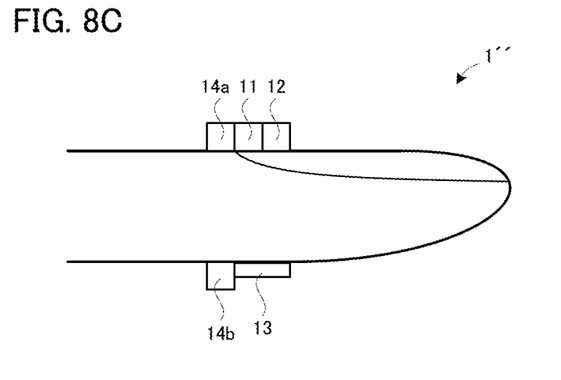

Regarding the light emitting device 11, the light emitting device 12, the light receiving device 13, and the mounting pressure detecting device 14, for example, as illustrated in FIG. 8A, the light emitting devices 11 and 12 may be placed on the back of a finger, and the light receiving device 13 and the mounting pressure detecting device 14 may be placed on the ball of the finger. Alternatively, as illustrated in FIG. 8B, the light emitting devices 11 and 12 and the mounting pressure detecting device 14 may be placed on the back of the finger, and the light receiving device 13 may be placed on the ball of the finger. Alternatively, as illustrated in FIG. 8C, the light emitting devices 11 and 12 and a mounting pressure detecting device 14a may be placed on the back of the finger, and the light receiving device 13 and a mounting pressure detecting device 14b may be placed on the ball of the finger.

Figure 9A:
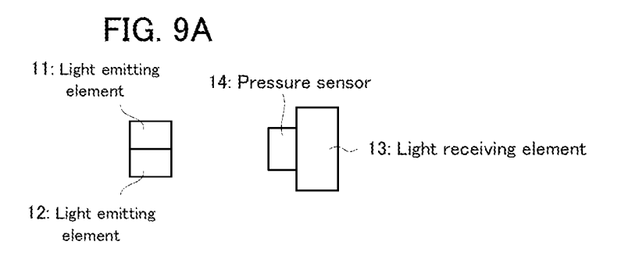
FIG. 9A to FIG. 9C are diagrams illustrating arrangement examples of elements that constitute a reflection type pulse oximeter according to the first example.
Figure 9B:
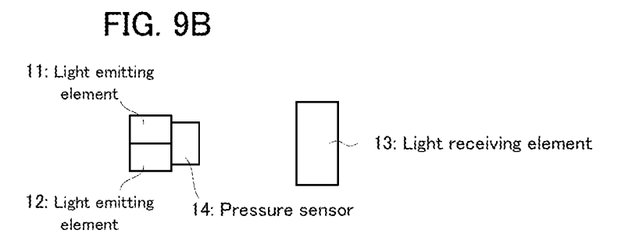
Figure 9C:
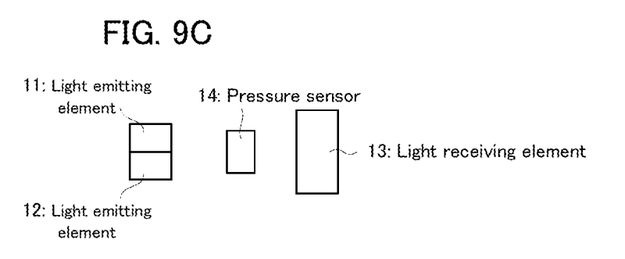

In the example, the transmission type pulse oximeter 1 was explained; however, the present invention can be applied to a reflection type pulse oximeter. In this case, the light emitting devices 11 and 12, the light receiving device 13, and the mounting pressure detecting device 14 can adopt, for example, any of arrangements illustrated in FIG. 9A to FIG. 9C.

The "light emitting device 11", the "light emitting device 12", the "light receiving device 13", the "mounting pressure detecting device 14", and the "calculating apparatus 100" are respectively one example of the "first light emitter", the "second light emitter", the "light receiver", the "contact pressure detecting device", and the "outputting device" according to the present invention.

In the example, as illustrated in FIG. 2, the amplification factor of the signal caused by the second transmitted light is changed. Instead of the signal caused by the second transmitted light, the amplification factor of the signal caused by the first transmitted light may be changed, or the amplification factors of both of the signal caused by the first transmitted light and the signal caused by the second transmitted light may be changed.

Modified Example

Figure 10:
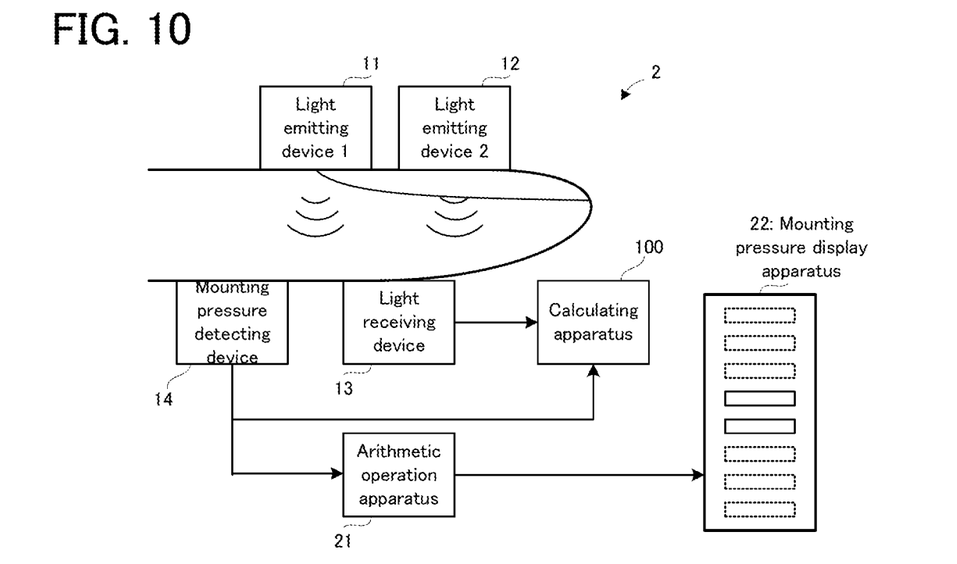
FIG. 10 is a schematic block diagram illustrating an outline of a pulse oximeter according to a modified example of the first example.

Next, a pulse oximeter according to a modified example of the first example will be explained with reference to FIG. 10. FIG. 10 is a schematic block diagram illustrating an outline of the pulse oximeter according to the modified example of the first example.

In FIG. 10, a pulse oximeter 2 according to the modified example of the first example is provided with an arithmetic operation apparatus 21 and a mounting pressure display apparatus 22, in addition to the light emitting device 11, the light emitting device 12, the light receiving device 13, the mounting pressure detecting device 14, and the calculating apparatus 100.

The arithmetic operation apparatus 21, which is one example of the "second outputting device" according to the present invention, outputs information regarding adjustment of the mounting pressure, which is suitable for display on the mounting pressure display device 22, on the basis of the signal outputted from the mounting pressure detecting device 14. Here, in particular, the display is performed in such a manner that the mounting pressure is guided into a predetermined range on the mounting pressure display device 22.

If a user of the pulse oximeter 2 adjusts the mounting pressure of the pulse oximeter 2 with reference to the display on the mounting pressure display device 22, the value of $SpO_2$ can be preferably measured.

Particularly if the mounting pressure is relatively high, for example, as illustrated in FIG. 7, a correction amount is relatively large. Thus, by virtue of the above configuration, errors caused by the correction can be suppressed, which is extremely useful in practice.

Second Example

A pulse oximeter according to a second example of the present invention will be explained with reference to FIG. 11. The second example is the same as the aforementioned first example, expect that the configuration of the pulse oximeter is partially different. Thus, the same explanation as that in the first example will be omitted, and the same parts will carry the same reference numerals. Basically, only a different point will be explained with reference to FIG. 11.

Figure 11:
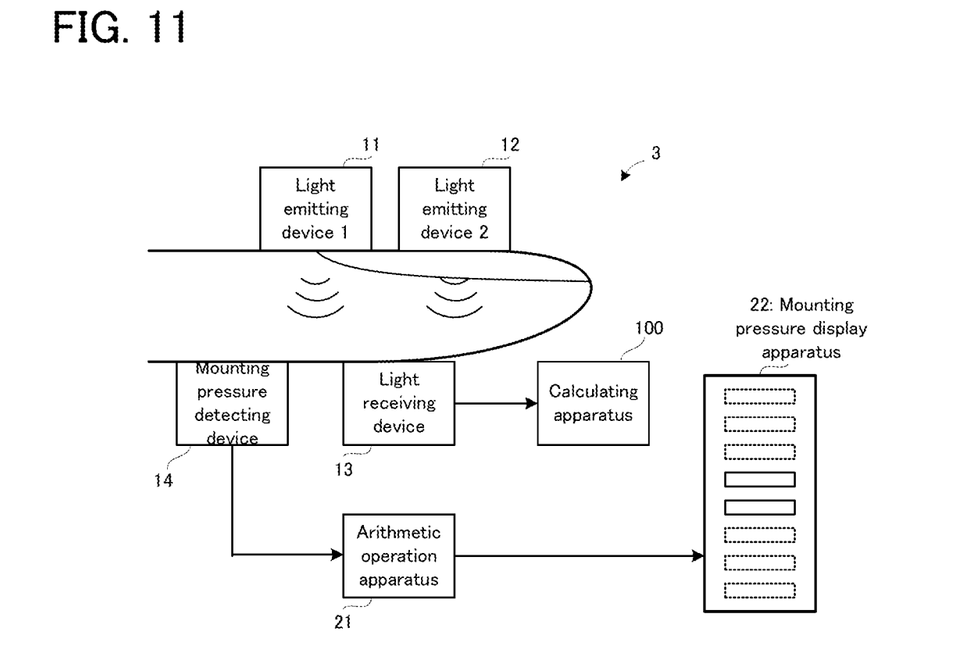
FIG. 11 is a schematic block diagram illustrating an outline of a pulse oximeter according to a second example.

In FIG. 11, a pulse oximeter 3 according to the second example is provided with the light emitting device 11, the light emitting device 12, the light receiving device 13, the mounting pressure detecting device 14, the arithmetic operation apparatus 21, the mounting pressure display device 22, and the calculating apparatus 100.

The arithmetic operation apparatus 21 outputs the information regarding the adjustment of the mounting pressure, which is suited for the display on the mounting pressure display device 22, on the basis of the signal outputted from the mounting pressure detecting device 14.

If a user of the pulse oximeter 3 adjusts the mounting pressure of the pulse oximeter 3 with reference to the display on the mounting pressure display device 22, the value of $SpO_2$ can be preferably measured, without the correction of the signal outputted from the light receiving device 13 as described in the first example.

Modified Example

Figure 12:
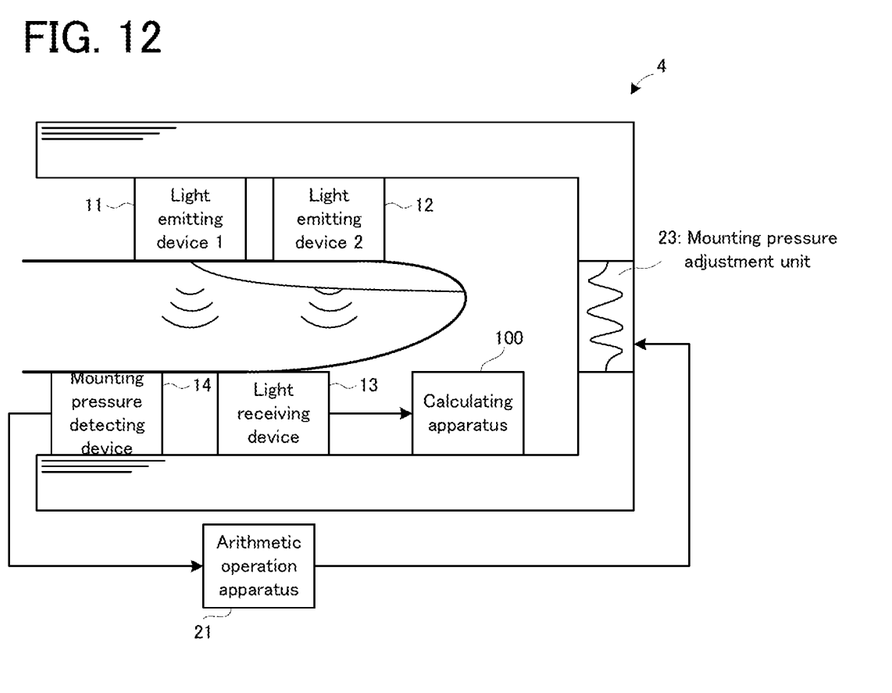
FIG. 12 is a schematic block diagram illustrating an outline of a pulse oximeter according to a modified example of the second example.

Next, a pulse oximeter according to a modified example of the second example will be explained with reference to FIG. 12. FIG. 12 is a schematic block diagram illustrating an outline of the pulse oximeter according to the modified example of the second example.

In FIG. 12, a pulse oximeter 4 according to the modified example of the second example is provided with a mounting pressure adjuster 23, in addition to the light emitting device 11, the light emitting device 12, the light receiving device 13, the mounting pressure detecting device 14, the arithmetic operation apparatus 21, and the calculating apparatus 100.

The mounting pressure adjuster 23 is mounted between a support member configured to support the light emitting devices 11 and 12 and a support member configured to support the light receiving device 13 and the mounting pressure detecting device 14.

The arithmetic operation apparatus 21 controls the mounting pressure adjuster 23 in accordance with the signal outputted from the mounting pressure detecting device 14, in such a manner that the mounting pressure has a predetermined value. By virtue of such configuration, the value of $SpO_2$ can be preferably measured.

The "arithmetic operation apparatus 21" and the "mounting pressure adjuster 23" are one example of the "adjusting device" according to the present invention.

The present invention is not limited to the aforementioned embodiments and examples, but various changes may be made, if desired, without departing from the essence or spirit of the invention which can be read from the claims and the entire specification. A pulse oximeter which involves such changes is also intended to be within the technical scope of the present invention.

DESCRIPTION OF REFERENCE NUMERALS 1, 2, 3, 4 pulse oximeter
11, 12 light emitting device
13 light receiving device
14, 14a, 14b mounting pressure detecting device
21 arithmetic operation apparatus
22 mounting pressure display apparatus
23 mounting pressure adjuster
100 calculating apparatus

The invention claimed is:

1. A pulse oximeter, comprising:
a first light emitter configured to generate a first light with a wavelength that is superior in absorption into oxygenated hemoglobin;
a second light emitter configured to generate a second light with a wavelength that is superior in absorption into deoxygenated hemoglobin and different;
a light receiver configured to receive each of a first return light of the first light from a living body and a second return light of the second light from the living body;
a contact pressure detecting device configured to detect a signal associated with contact pressure between said pulse oximeter and the living body;
an amplifier configured to amplify one of a first signal outputted from the light receiver due to the first return light and a second signal outputted from the light receiver due to the second return light with an amplification factor according to a magnitude of contact pressure indicated by the detected signal associated with the contact pressure; and
an outputting device configured to output information regarding oxygen saturation, based on i) the amplified one of the first signal and the second signal outputted from the amplifier and ii) the other of the first signal and the second signal.

2. The pulse oximeter according to claim 1, further comprising:
a second outputting device configured to output information associated with adjustment of the contact pressure in accordance with the detected signal associated with the contact pressure.

* * * * *